(12) United States Patent
Onuma et al.

(10) Patent No.: US 9,814,859 B2
(45) Date of Patent: Nov. 14, 2017

(54) VEHICLE SEAT

(71) Applicant: TOYOTA JIDOSHA KABUSHIKI KAISHA, Toyota-shi, Aichi-ken (JP)

(72) Inventors: Masahiko Onuma, Toyota (JP); Kouji Saitou, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 15/209,856

(22) Filed: Jul. 14, 2016

(65) Prior Publication Data

US 2017/0028163 A1   Feb. 2, 2017

(30) Foreign Application Priority Data

Jul. 30, 2015   (JP) .................................. 2015-150924

(51) Int. Cl.
*G08B 23/00* (2006.01)
*A61M 21/00* (2006.01)
(Continued)

(52) U.S. Cl.
CPC ........... *A61M 21/00* (2013.01); *A61H 9/0078* (2013.01); *A61H 23/02* (2013.01); *A61H 23/04* (2013.01); *B60N 2/448* (2013.01); *B60N 2/4415* (2013.01); *B60W 40/09* (2013.01); *B60W 50/16* (2013.01); *G05D 1/0061* (2013.01); *A61H 2201/0149* (2013.01); *A61H 2201/1207* (2013.01); *A61H 2201/5002* (2013.01); *A61H 2201/503* (2013.01); *A61H 2205/081* (2013.01); *A61H 2205/108* (2013.01); *A61H 2230/065* (2013.01);
(Continued)

(58) Field of Classification Search
CPC .......... A61M 21/00; A61M 2021/0022; A61H 9/0078; A61H 2201/5002; B60N 2/448; B60N 2002/4485; B60N 2/665
USPC .................................. 340/575, 576; 601/150
See application file for complete search history.

(56) References Cited

U.S. PATENT DOCUMENTS

| 7,727,171 B2* | 6/2010 | Ozaki | A61H 9/0078 297/284.3 |
| 8,162,398 B2* | 4/2012 | Colja | A61H 9/0078 297/284.4 |
| 8,608,243 B2* | 12/2013 | Maeda | B60N 2/66 297/217.3 |

(Continued)

FOREIGN PATENT DOCUMENTS

| JP | H05-330360 A | 12/1993 |
| JP | H10-278541 A | 10/1998 |

(Continued)

*Primary Examiner* — Toan N Pham
(74) *Attorney, Agent, or Firm* — Oliff PLC (57) ABSTRACT

A vehicle seat includes: plural airbags for massaging that are provided at least at an interior of a seatback, and that inflate to push against portions of a body of a seated vehicle occupant; an air supplying/discharging device that has a forced-air source that feeds air under pressure, and a control valve that supplies and discharges the air, that has been fed under pressure from the forced-air source, to the plural airbags respectively, so that the air supplying/discharging device inflates and contracts the plural airbags individually; and an electronic control unit that, in a state in which the forced-air source is operated, repeats, at a uniform cycle, supplying and discharging of the air by switching of the control valve, to generate awakening vibrations at least at one airbag among the plural airbags.

9 Claims, 7 Drawing Sheets (51) Int. Cl.
*A61H 9/00* (2006.01)
*B60N 2/44* (2006.01)
*A61H 23/04* (2006.01)
*B60W 40/09* (2012.01)
*B60W 50/16* (2012.01)
*G05D 1/00* (2006.01)
*A61H 23/02* (2006.01)
*B60W 40/08* (2012.01)

(52) U.S. Cl.
CPC ............... *A61M 2021/0022* (2013.01); *A61M 2021/0083* (2013.01); *A61M 2205/50* (2013.01); *A61M 2230/06* (2013.01); *A61M 2230/42* (2013.01); *B60N 2002/4485* (2013.01); *B60W 2040/0827* (2013.01)

(56) References Cited

U.S. PATENT DOCUMENTS

| | | | |
|---|---|---|---|
| 9,504,416 B2 * | 11/2016 | Young | B60N 2/0276 |
| 9,527,421 B2 * | 12/2016 | Hulway | B60N 2/643 |
| 2006/0049678 A1 * | 3/2006 | Kern | A47C 7/467 |
| | | | 297/284.3 |
| 2006/0217644 A1 | 9/2006 | Ozaki et al. | |
| 2011/0068611 A1 | 3/2011 | Maeda et al. | |

FOREIGN PATENT DOCUMENTS

| | | | |
|---|---|---|---|
| JP | 2006-198070 A | 8/2006 | |
| JP | 2014-212976 A | 11/2014 | |

* cited by examiner

VEHICLE SEAT

CROSS-REFERENCE TO RELATED APPLICATION

This application is based on and claims priority under 35 USC 119 from Japanese Patent Application No. 2015-150924 filed on Jul. 30, 2015, the entire contents of which is incorporated by reference herein.

BACKGROUND

Technical Field

The present disclosure relates to a vehicle seat that can impart an awakening effect to a seated vehicle occupant.

Related Art

Vehicle seats that are equipped with a vibration generating device for imparting a massaging effect or an awakening effect to a seated vehicle occupant are known (see, for example, Japanese Patent Application Laid-Open (JP-A) No. 2014-212976 (Patent Document 1)).

However, in a case in which a vibration generating device that imparts an awakening effect to a seated vehicle occupant is provided at a vehicle seat that has plural airbags that impart a relaxing effect (a refreshing effect) to the seated vehicle occupant by inflating and pressing portions of the body of the seated vehicle occupant, the problem arises that the space for the setting of the vibration generating device is insufficient.

SUMMARY

Thus, an object of the present disclosure is to provide a vehicle seat that can impart a relaxing effect and can also impart an awakening effect to a seated vehicle occupant.

In order to achieve the above-described object, a vehicle seat relating to a first aspect of the present disclosure includes: plural airbags for massaging that are provided at least at an interior of a seatback, and that inflate to push portions of a body of a seated vehicle occupant; an air supplying/discharging device that has a forced-air source that feeds air under pressure, and a control valve that supplies and discharges the air, that has been fed under pressure from the forced-air source, to the plural airbags respectively, so that the air supplying/discharging device inflates and contracts the plural airbags individually; and an electronic control unit that, in a state in which the forced-air source is operated, repeats, at a uniform cycle, supplying and discharging of the air by switching of the control valve, to generate awakening vibrations at least at one airbag among the plural airbags.

In accordance with the first aspect, a seated vehicle occupant is made to relax due to the plural airbags for massaging, that are provided at least at the interior of the seatback, individually inflating to push against portions of the body of the seated vehicle occupant. Further, in a state in which the forced-air source is operated, the supplying and discharging of air due to switching of the control valve is repeated at a uniform cycle by the control of the electronic control unit, and awakening vibrations are generated at least at one airbag among the plural airbags.

Namely, vibrations that awaken the seated vehicle occupant are imparted by the airbags that are used to relax the seated vehicle occupant. Accordingly, setting space for the provision of a vibration generating device that imparts an awakening effect to the seated vehicle occupant is unnecessary, and not only a relaxing effect, but also an awakening effect can be imparted to the seated vehicle occupant.

Further, in a vehicle seat relating to a second aspect, which includes the vehicle seat relating to the first aspect, the electronic control unit generates the awakening vibrations at the at least one airbag when it is detected that the seated vehicle occupant is tending toward falling asleep.

In accordance with the second aspect, when a seated vehicle occupant is tending toward falling asleep, an awakening effect can be imparted to that seated vehicle occupant who is tending toward falling asleep.

In a vehicle seat relating to a third aspect, which includes the vehicle seat relating to the first aspect, the electronic control unit generates the awakening vibrations at the at least one airbag at a time of an automatic driving mode of a self-driving vehicle, when it is detected that the seated vehicle occupant is tending toward falling asleep or is in a state of falling asleep.

In accordance with the third aspect, at the time of an automatic driving mode of a self-driving vehicle, when there is the need to awaken the seated vehicle occupant such as at a time when the seated vehicle occupant is tending toward falling asleep or is in a state of falling asleep and switching to a manual driving mode is to be carried out, or the like, an awakening effect can be imparted to the seated vehicle occupant who is tending toward falling asleep or is in a state of falling asleep.

Further, in a vehicle seat relating to a fourth aspect, which includes the vehicle seat relating to any one of the first through third aspects, the electronic control unit vibrates the plural airbags with the awakening vibrations at a predetermined timing and in a predetermined order.

In accordance with the fourth aspect, the plural airbags are vibrated with the awakening vibrations at a predetermined timing and in a predetermined order, by control of the electronic control unit. Accordingly, an awakening effect can be effectively imparted to the seated vehicle occupant (the seated vehicle occupant who is tending toward falling asleep). Further, at the time of an automatic driving mode of a self-driving vehicle, when the seated vehicle occupant is tending toward falling asleep or is in a state of falling asleep and there is the need to awaken the seated vehicle occupant, an awakening effect can be effectively imparted to that seated vehicle occupant who is tending toward falling asleep or is in a state of falling asleep.

Further, in a vehicle seat relating to a fifth aspect, which includes the vehicle seat relating to any one of the first through third aspects, the electronic control unit vibrates the plural airbags with the awakening vibrations at a predetermined timing and in a random order.

In accordance with the fifth aspect, the plural airbags are vibrated with the awakening vibrations at a predetermined timing and in a random order, by control of the electronic control unit. Accordingly, an awakening effect can be more effectively imparted to the seated vehicle occupant (the seated vehicle occupant who is tending toward falling asleep). Further, at the time of an automatic driving mode of a self-driving vehicle, when the seated vehicle occupant is tending toward falling asleep or is in a state of falling asleep and there is the need to awaken the seated vehicle occupant, an awakening effect can be more effectively imparted to that seated vehicle occupant who is tending toward falling asleep or is in a state of falling asleep.

In accordance with the first aspect, a relaxing effect can be imparted and an awakening effect can also be imparted to a seated vehicle occupant.

In accordance with the second aspect, when a seated vehicle occupant is tending toward falling asleep, an awakening effect can be imparted to that seated vehicle occupant who is tending toward falling asleep.

In accordance with the third aspect, at the time of an automatic driving mode of a self-driving vehicle, when a seated vehicle occupant is tending toward falling asleep or is in a state of falling asleep and there is the need to awaken the seated vehicle occupant, an awakening effect can be imparted to the seated vehicle occupant who is tending toward falling asleep or is in a state of falling asleep.

In accordance with the fourth aspect, an awakening effect can be effectively imparted to a seated vehicle occupant (a seated vehicle occupant who is tending toward falling asleep), and further, at the time of an automatic driving mode of a self-driving vehicle, when the seated vehicle occupant is tending toward falling asleep or is in a state of falling asleep and there is the need to awaken the seated vehicle occupant, an awakening effect can be effectively imparted to the seated vehicle occupant who is tending toward falling asleep or is in a state of falling asleep.

In accordance with the fifth aspect, an awakening effect can be more effectively imparted to a seated vehicle occupant (a seated vehicle occupant who is tending toward falling asleep), and further, at the time of an automatic driving mode of a self-driving vehicle, when the seated vehicle occupant is tending toward falling asleep or is in a state of falling asleep and there is the need to awaken the seated vehicle occupant, an awakening effect can be more effectively imparted to the seated vehicle occupant who is tending toward falling asleep or is in a state of falling asleep.

DETAILED DESCRIPTION

An embodiment is described in detail hereinafter on the basis of the drawings. Note that, for convenience of explanation, arrow UP that is shown appropriately in the respective drawings is the upward direction of a vehicle seat 10 (of a self-driving vehicle 60), arrow FR is the frontward direction of the vehicle seat 10 (of the self-driving vehicle 60), and arrow RH is the rightward direction of the vehicle seat 10 (of the self-driving vehicle 60). Accordingly, in the following description, when vertical, longitudinal and left-right directions are used without being specified, they refer to the vertical of the vertical direction (of the vehicle), the longitudinal of the longitudinal direction (of the vehicle) and the left and right of the left-right direction at the vehicle seat 10 (of the self-driving vehicle 60).

Figure 1:
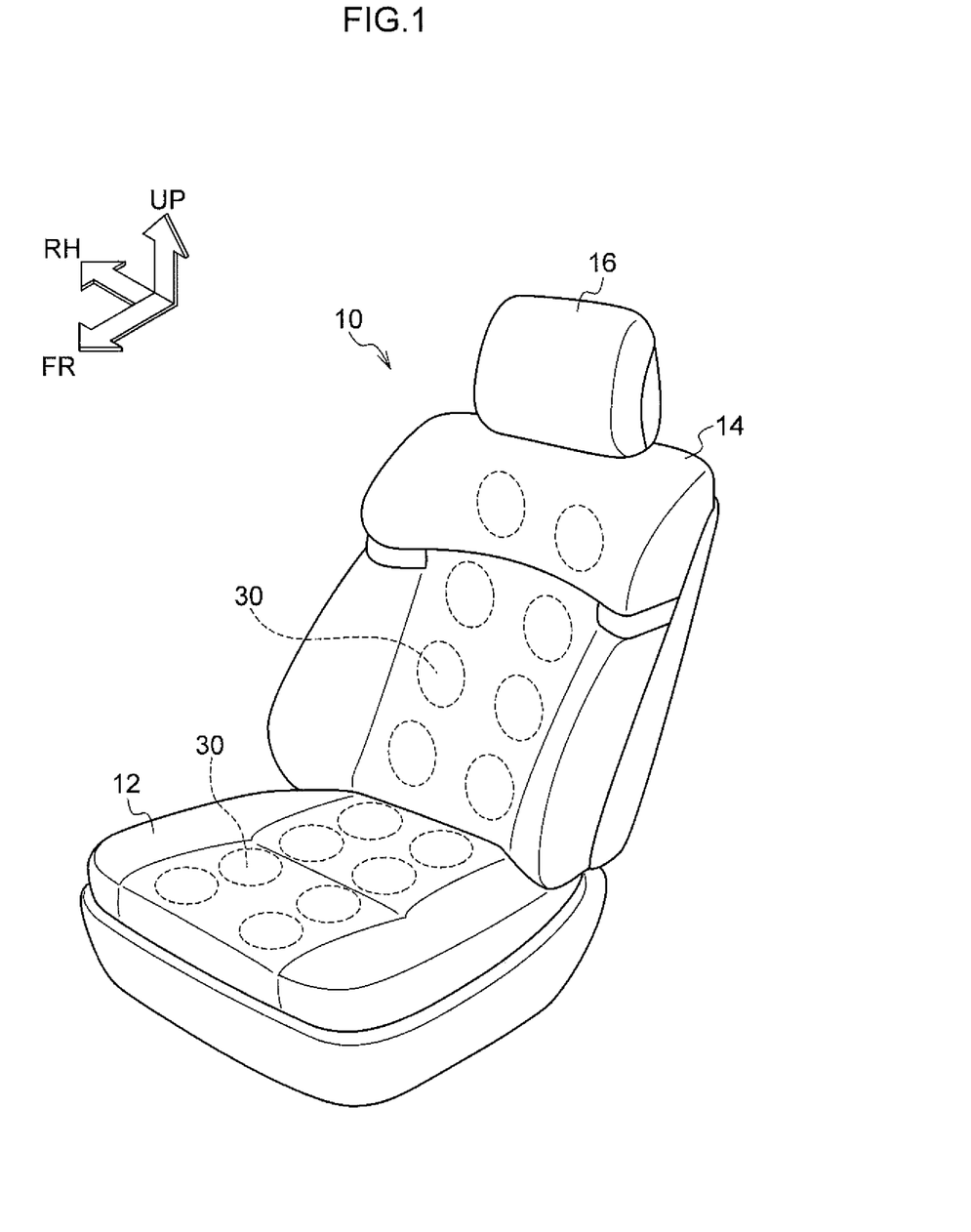
FIG. 1 is a perspective view showing a vehicle seat relating to a present embodiment.

First, the overall structure of the vehicle seat 10 relating to the present embodiment is described. As shown in FIG. 1, the vehicle seat 10 has a seat cushion 12 that supports the buttocks and femoral region of a seated vehicle occupant (hereinafter called "the driver" as an example), and a seatback 14 that is provided so as to extend upward from the rear end portion of the seat cushion 12 and that supports the lumbar region and the back portion of the driver. Further, a headrest 16 that supports the head portion of the driver is provided at the upper end portion of the seatback 14.

Plural airbags 30 that are respectively for massaging (refreshing) are provided at the interiors of the seat cushion 12 and the seatback 14 of the vehicle seat 10. Due to the respective airbags 30 inflating and pushing portions of the driver's body, the airbags 30 massage the lumbar region or the back portion and the femoral region or the like of the driver, and relax (refresh) the driver.

Note that the airbags 30 within the seatback 14 are, for example, disposed in the vertical direction in two rows, and the airbags 30 within the seat cushion 12 are, for example, disposed in the longitudinal direction in two rows (see FIG. 1). Because the respective airbags 30 have the same structures, here, description is given by using the airbag 30 within the seatback 14 as an example.

Figure 2:
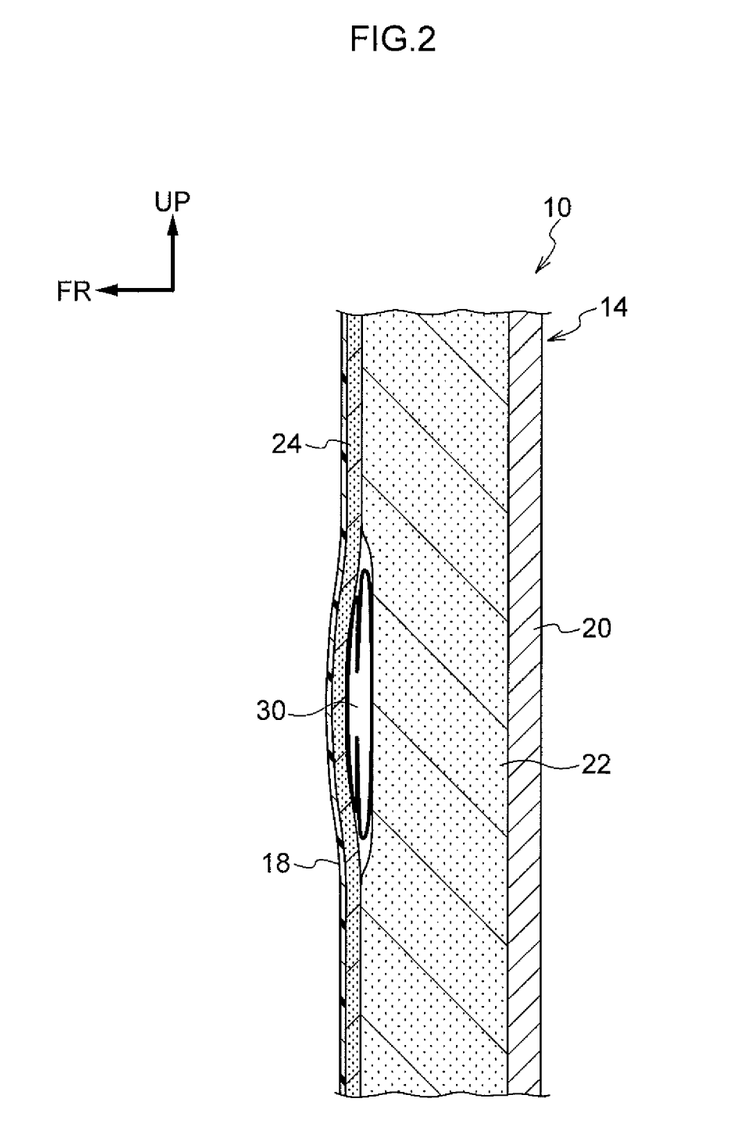
FIG. 2 is a cross-sectional view showing a state in which an airbag, that is provided at the vehicle seat relating to the present embodiment, is contracted.
Figure 3:
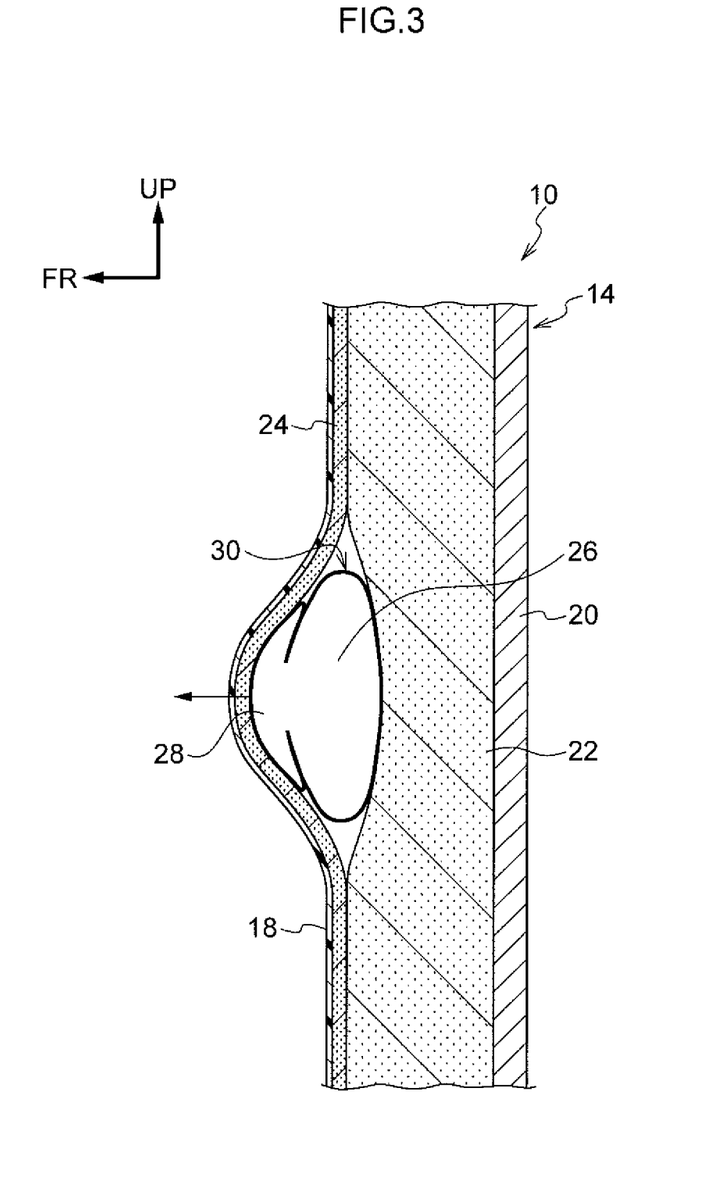
FIG. 3 is a cross-sectional view showing a state in which the airbag, that is provided at the vehicle seat relating to the present embodiment, is inflated.

As shown in FIG. 2 and FIG. 3, the seatback 14 has a seat frame 20, a seat pad 22 that is disposed at the driver's side (hereinafter also called "obverse side" upon occasion) of the seat frame 20, a slab 24 that is shaped as a sheet and is disposed at the obverse side of the seat pad 22, and a skin 18 that covers the obverse side of the slab 24.

The seat pad 22 is formed from a cushion body, and is structured by a foamed resin such as foamed urethane or the like for example. The slab 24 is softer than the seat pad 22, and is structured from a material that can elastically (flexurally) deform, e.g., a foamed resin such as foamed urethane or the like whose void ratio is different than that of the seat pad 22.

Note that the slab 24 is provided in order to make the seating comfort of the vehicle seat 10 better. Further, the skin 18 also structures the design surface of the vehicle seat 10. The respective airbags 30 are provided between the seat pad 22 and the slab 24 due to the back surfaces (the surfaces that are at the obverse-reverse opposite sides of the obverses thereof) being fixed by double-sided tape or an adhesive to the obverse side of the seat pad 22.

Each of the airbags 30 is structured from an expandable/contractible material such as a resin material such as polyurethane or the like, or a rubber material, or the like. As shown in FIG. 1 through FIG. 3, each of the airbags 30 is structured to include a large diameter portion 26 that is substantially circular in a front view seen from the front direction, and a small diameter portion 28 that communicates with the large diameter portion 26. Note that the large diameter portion 26 is fixed to the obverse side of the seat pad 22, and the small diameter portion 28 is disposed at the slab 24 side.

Figure 4:
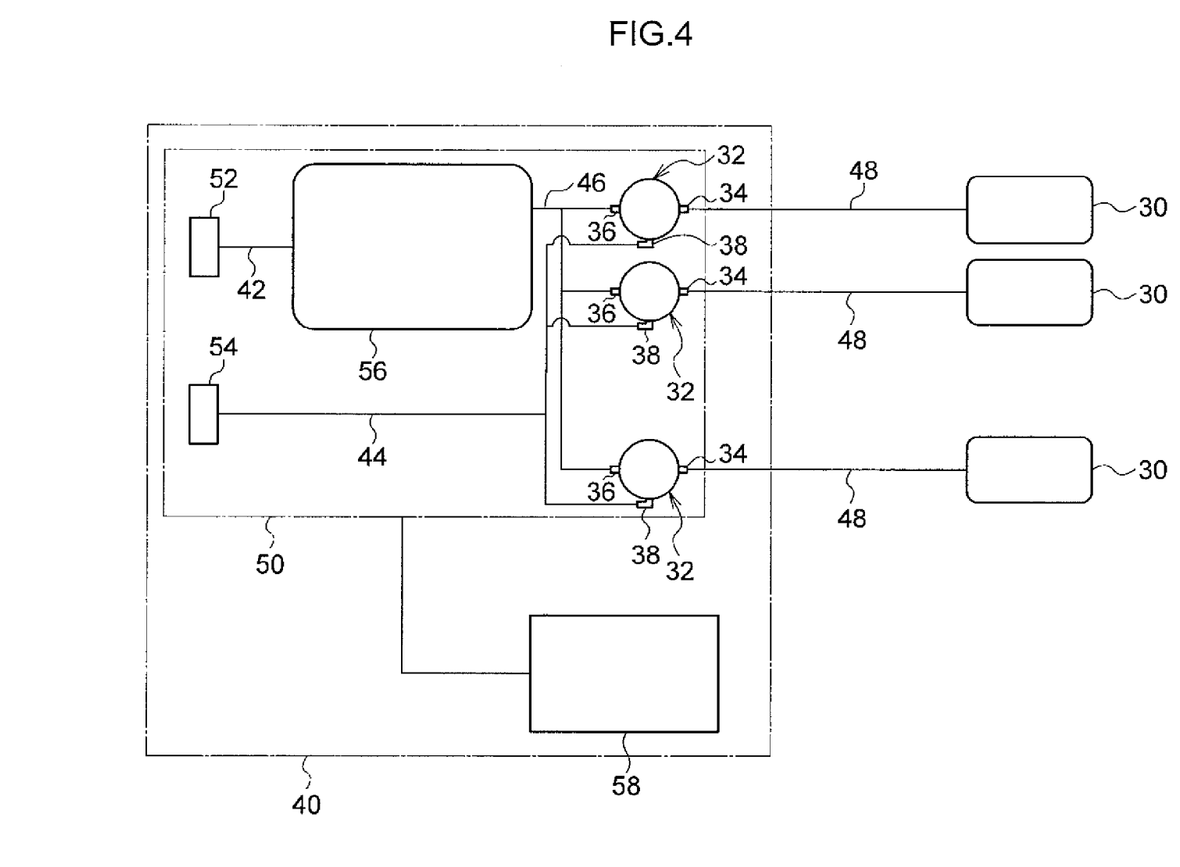
FIG. 4 is a block diagram showing an airbag driving device that is provided at the vehicle seat relating to the present embodiment.

Here, an airbag driving device 40, that has an air supplying/discharging device 50 that carries out the supplying and discharging of air to and from the respective airbags 30 and that inflates and contracts the respective airbags 30 individually, is described on the basis of FIG. 4.

As shown in FIG. 4, the airbag driving device 40 is structured to include the air supplying/discharging device 50 to which the respective airbags 30 are connected, and a control device (an Electronic Control Unit (ECU)) 58 that controls the air supplying/discharging device 50. The ECU (control device 58) is a microcomputer having a Central Processing Unit (CPU) and memory including RAM and ROM. The air supplying/discharging device 50 is structured to include an intake opening 52, an exhaust opening 54, a pump 56 that serves as an air force-feeding means, and plural electromagnetic valves 32 that serve as control valves.

One electromagnetic valve 32 is provided for each airbag 30. Each of the electromagnetic valves 32 is a three-way valve, and has a common port 34, an intake port 36 and an exhaust port 38. Common tubes 48 are connected to the respective common ports 34, and an intake tube 46 is connected to the respective intake ports 36. Further, an exhaust tube 44 is connected to the respective exhaust ports 38.

The respective common tubes 48 are connected to the corresponding airbags 30, and the intake tube 46 is connected to the pump 56. Further, the exhaust tube 44 is connected to the exhaust opening 54. An intake pipe 42 is connected between the pump 56 and the intake opening 52 so as to communicate therewith. Note that the intake tube 46 and the exhaust tube 44 are each structured by a single tube being branched-off and connected to the respective electromagnetic valves 32.

The control device 58 is electrically connected to the air supplying/discharging device 50, and controls the operation of the pump 56, and the opening/closing of the respective ports (the common ports 34, the intake ports 36, the exhaust ports 38) of the electromagnetic valves 32. Note that the control device 58 is structured so as to be able to individually control the opening/closing of the respective ports (the common ports 34, the intake ports 36, the exhaust ports 38) of the respective electromagnetic valves 32.

Further, the control device 58 is electrically connected to an operation portion (not illustrated) that is operated by the driver who is seated in the vehicle seat 10. Accordingly, due to the driver operating the operation portion, the inflation and contraction of the plural (some or all) of the airbags 30 are repeated individually and intermittently.

Concretely, when, due to the control of the control device 58, there is a supplying state in which the common port 34 and the intake port 36 of the electromagnetic valve 32 are open and the exhaust port 38 is closed and the common tube 48 and the intake tube 46 communicate with one another, air is supplied from the pump 56 to the airbag 30 interior, and, as shown in FIG. 3, the airbag 30 inflates.

Further, when, due to the control of the control device 58, there is an exhausting state in which the common port 34 and the exhaust port 38 of the electromagnetic valve 32 are open and the intake port 36 is closed and the common tube 48 and the exhaust tube 44 communicate with one another, air is discharged from the airbag 30 interior, and, as shown in FIG. 2, the airbag 30 contracts.

Note that, because the slab 24 is softer than the seat pad 22 and is structured from a material that can elastically (flexurally) deform, when the airbag 30 inflates, the slab 24 and the skin 18 are made to bulge-out toward the vehicle body front side. Further, the airbag driving device 40 (the air supplying/discharging device 50 and the control device 58) are disposed within the seatback 14 or within the seat cushion 12.

Operation of the vehicle seat 10, that relates to the present embodiment and is structured as described above, is described next.

Due to the driver, who is seated in the vehicle seat 10 illustrated in FIG. 1, operating the operation portion, the airbag driving device 40 shown in FIG. 4 is driven. Namely, a massaging operation (a massage mode) for the driver is started. Note that, at usual times (at times other than the massaging operation), the electromagnetic valves 32 are controlled by the control device 58 to be in exhausting states. Namely, the respective airbags 30 are in the contracted state shown in FIG. 2.

When the massaging operation is started, the pump 56 operates due to control of the control device 58. Further, at the airbag 30 that is in the supplying state in which the exhaust port 38 of the electromagnetic valve 32 is closed and the common port 34 and the intake port 36 are open, air that is taken-in from the intake opening 52 via the intake pipe 42 is supplied via the intake tube 46, the electromagnetic valve 32 and the common tube 48, and the airbag 30 inflates as shown in FIG. 3. Namely, the slab 24 and the skin 18 bulge-out and press the lumbar region or the back portion and the femoral region or the like of the seated driver.

Thereafter, operation of the pump 56 stops, and, at the airbag 30 that is inflated, the intake port 36 of the electromagnetic valve 32 closes and common port 34 and the exhaust port 38 open such that the airbag 30 is set in an exhausting state, and the air within the airbag 30 is exhausted, via the common tube 48, the electromagnetic valve 32 and the exhaust tube 44, from the exhausting opening 54, and the airbag 30 contracts as shown in FIG. 2. Namely, the slab 24 and the skin 18 return to their original states, and the pressing of the lumbar region or the back portion and the femoral region or the like of the seated driver is cancelled.

The above-described inflating and contracting operations are carried out repeatedly at a predetermined time difference (e.g., a difference of one to three seconds) at some of or all of the airbags 30. Due to the above operations, the lumbar region or the back portion and the femoral region or the like of the driver who is seated in the vehicle seat 10 is massaged, and a relaxing effect and a refreshing effect can be imparted to the driver.

Figure 6:
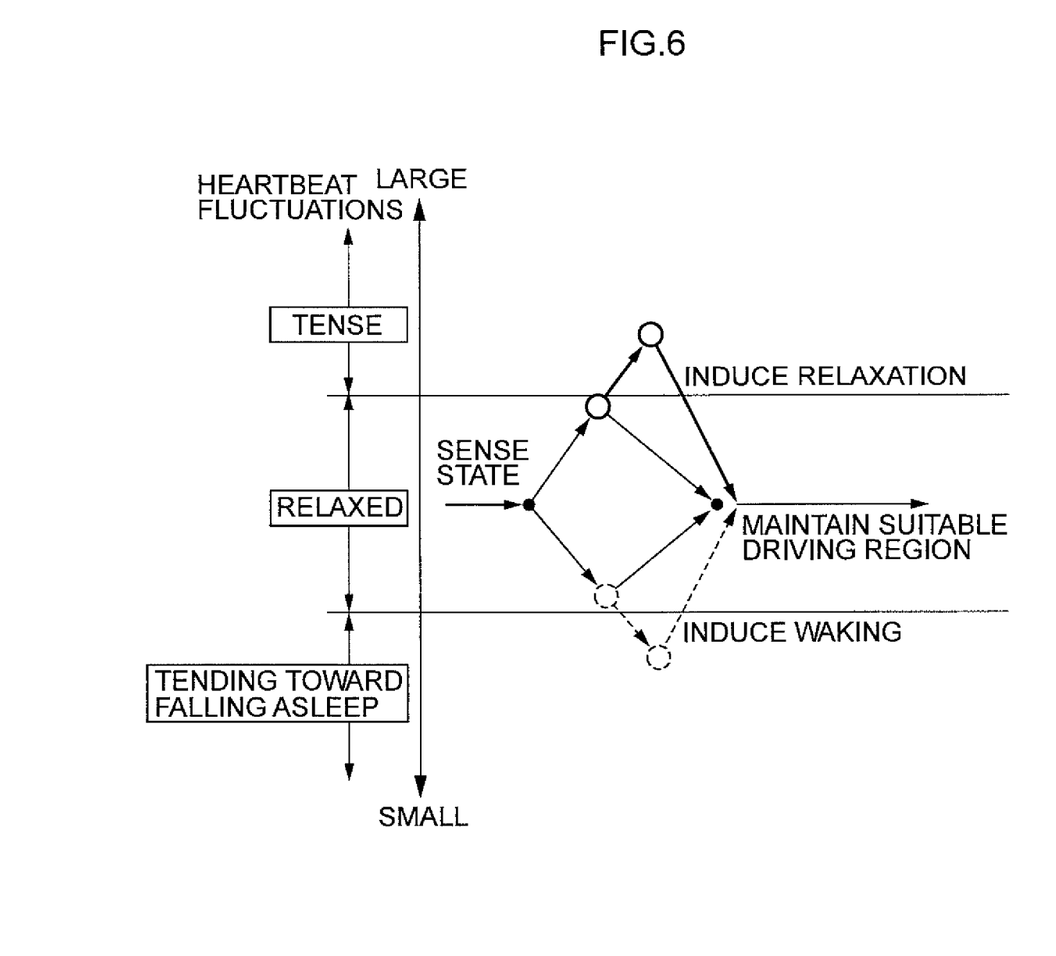
FIG. 6 is an explanatory drawing that shows conditions for vibrating the airbag that is provided at the vehicle seat relating to the present embodiment.

Namely, a region suitable for driving that is shown in FIG. 6 (a relaxed state that is detected from heartbeat fluctuations that are periodic fluctuations in the heartbeat interval) can be maintained for the driver. Note that the positions of the airbags 30 that are inflated and contracted, and the timing (the predetermined time difference) of causing the inflation and expansion of the airbags 30, and the like can be changed by the driver operating the operation portion.

Further, there may be a structure in which the state (the heartbeat fluctuations) of the driver who is in the midst of driving are sensed by a state detecting device (not illustrated) such as an in-vehicle camera (not illustrated) or a sensor or the like that senses biomedical signals (the respiratory rate or the heartbeat rate or the like) of the driver, and, as shown in FIG. 6, when it is detected that the driver is in a tense state (the heartbeat fluctuations are larger than in the region that is the relaxed state), the massaging operation is started automatically, rather than by the driver operating the operation portion.

Further, the state (the heartbeat fluctuations) of the driver who is in the midst of driving may be sensed by a state detecting device such as an in-vehicle camera or a sensor that senses biomedical signals of the driver or the like, and, as shown in FIG. 6, when it is detected that the driver is tending toward falling asleep (the heartbeat fluctuations are smaller than in the region that is the relaxed state), an awakening effect can be imparted to the driver who is tending toward falling asleep (a light sleep of an extent of being overcome by drowsiness), by using the airbags 30.

Figure 5:
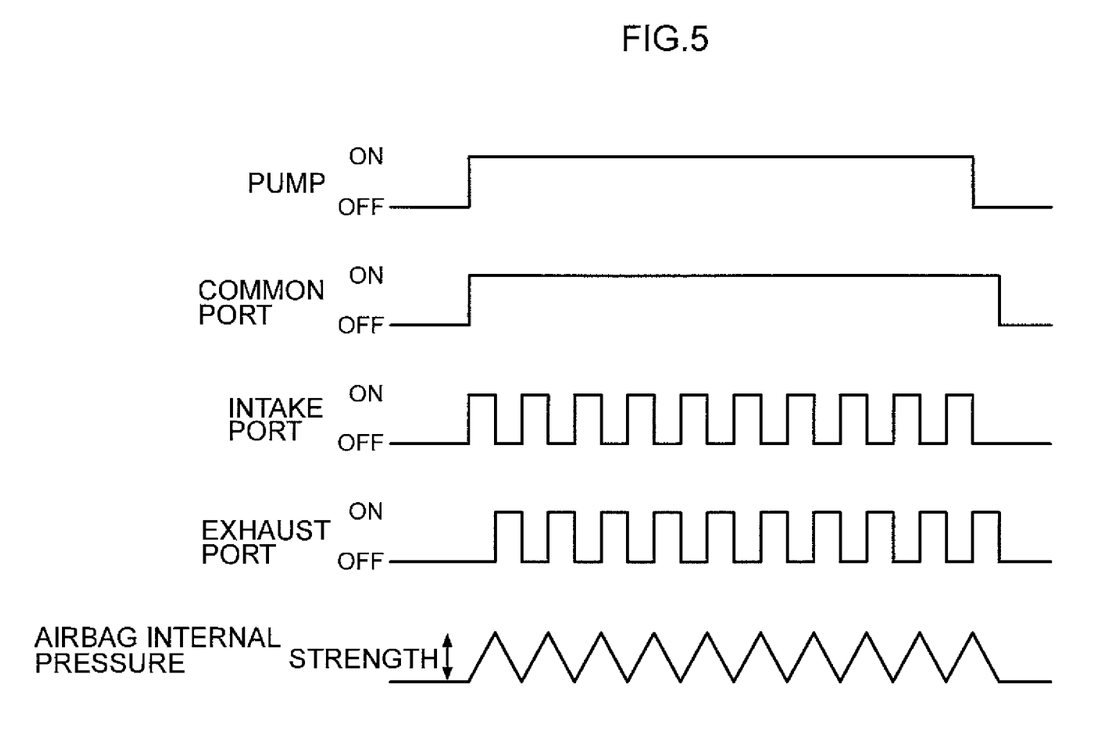
FIG. 5 is an explanatory drawing that shows timing charts for vibrating the airbag that is provided at the vehicle seat relating to the present embodiment, and the strength of pressure within the airbag.

Namely, due to the airbag driving device 40 being controlled by the control device 58 that is shown in FIG. 4, at least one predetermined airbag 30 is vibrated (hereinafter, this mode is called "awakening mode" upon occasion). Concretely, as shown in FIG. 5, the pump 56 and the common port 34 are set in an on (operated) state always, and the intake port 36 and the exhaust port 38 are alternately turned on (opened) and off (closed) at a predetermined timing (e.g., every 0.2 seconds).

Due to the above operations, the predetermined airbag 30 is inflated and contracted at a uniform cycle (e.g., a 0.2 second interval), and therefore, vibrations can be imparted to the driver who is tending toward falling asleep, and an awakening effect can be imparted to that driver. Accordingly, the driver can be effectively prevented from falling asleep at the wheel, and a suitable driving region (a relaxed state) can be maintained for the driver.

Note that the airbag 30 that is in the vicinity of the lumbar region, where it is easiest for the driver to fit closely to the seatback 14, is desirably selected as the predetermined airbag 30 that imparts vibrations to the driver. Further, the state detecting device detecting in this way that a driver who is in the midst of driving is tending toward falling asleep is an example of a condition under which the awakening mode is executed at the vehicle seat 10 relating to the present embodiment.

Figure 7:
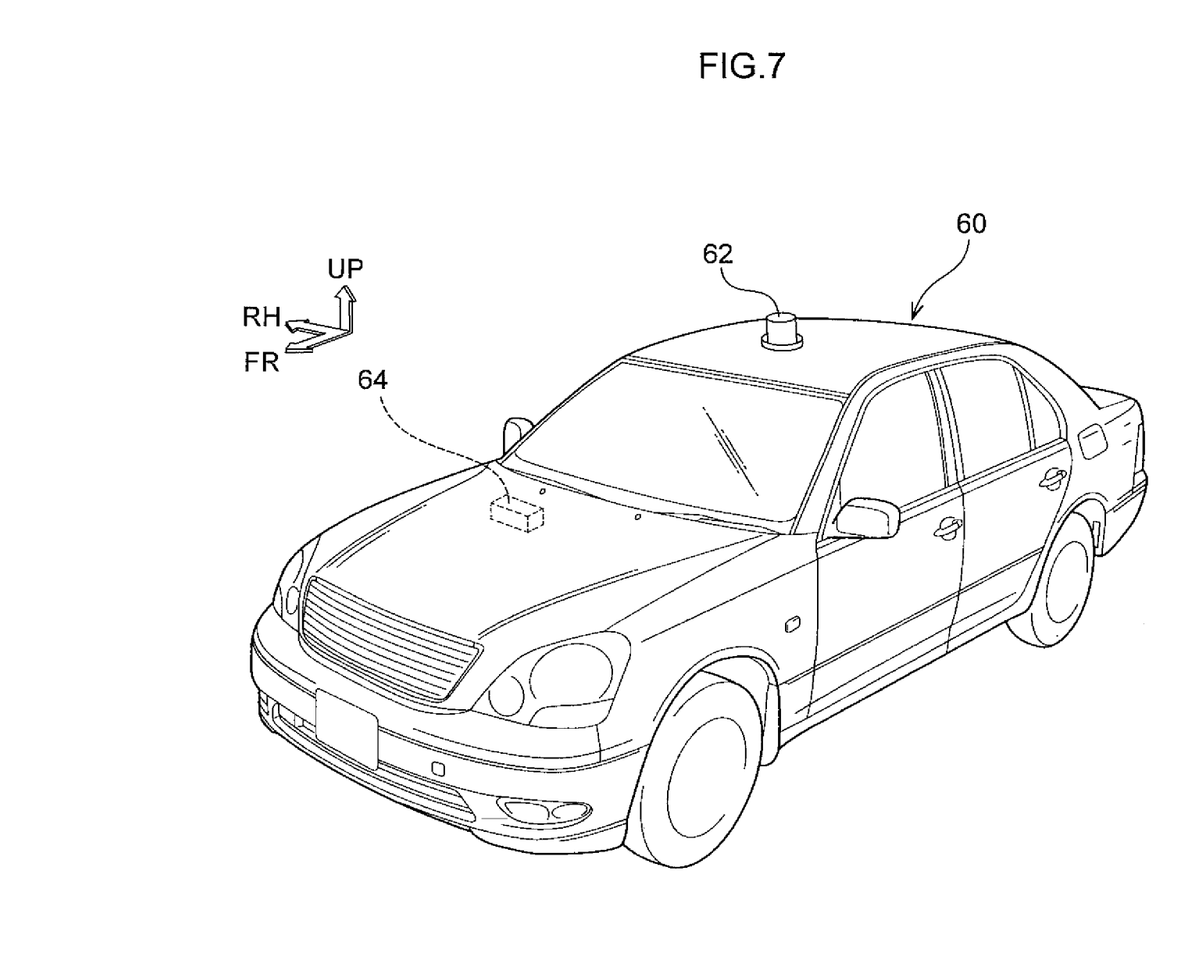
FIG. 7 is a perspective view showing a self-driving vehicle that has the vehicle seat relating to the present embodiment.

Further, in the self-driving vehicle 60 that is shown in FIG. 7, at times such as when the need arises to switch the driving mode from an automatic driving mode to a manual driving mode (including a driving support mode), or the like, the vehicle seat 10 relating to the present embodiment is effective also at times when an awakening effect is imparted to a driver who is in a state of falling asleep (who is in a deep sleep of the extent of a sound sleep) at the time of the automatic driving mode.

Namely, at the time of the automatic driving mode, the state detecting device, such as an in-vehicle camera or a sensor that senses biomedical signals of the driver or the like, detects that the driver is in a state of falling asleep, and, when a peripheral information detecting device 62 that is described later, or the like, detects that there is the need to switch to the manual driving mode such as when the vehicle arrives at its destination or the like for example, an awakening effect can be imparted to the driver who is in a state of falling asleep by causing the airbag 30 to vibrate as described above.

Note that "automatic driving mode" is a mode in which a controller 64 (see FIG. 7) (which includes an ECU) that is provided at the self-driving vehicle 60 drives the self-driving vehicle 60 on the basis of peripheral information, that is detected by the peripheral information detecting device 62 (see FIG. 7) that is provided at the self-driving vehicle 60, or the like. Further, "manual driving mode" is a mode in which the driver himself operates the steering wheel and the like and drives the self-driving vehicle 60.

In this way, at the time of the automatic driving mode of the self-driving vehicle 60, the state detecting device detecting that the driver is in a state of falling asleep (or is tending toward falling asleep), and the peripheral information detecting device 62 or the like detecting that there is the need to awaken the driver such as there is the need to switch to the manual driving mode or the like, is an example of a condition under which the awakening mode is executed.

Further, the plural airbags 30 that are disposed within the seatback 14 and within the seat cushion 12 may be made to vibrate at a predetermined timing and in a predetermined order, by the control of the control device 58. In accordance with such a structure, because the driver can, to a certain extent, predict which of the airbags 30 will vibrate, an awakening effect can be imparted effectively without imparting discomfort to a driver who is tending toward falling asleep (who is lightly sleeping) in particular.

Further, the plural airbags 30 that are disposed within the seatback 14 and within the seat cushion 12 may be made to vibrate at a predetermined timing and in a random order, by the control of the control device 58. In accordance with such a structure, because the driver cannot predict which of the airbags 30 will vibrate, the driver can be prevented from becoming used to the vibration of the airbag 30 at a fixed position. Accordingly, an awakening effect can be imparted more effectively to a driver who is in a state of falling asleep (who is in a deep sleep) in particular.

As described above, in accordance with the vehicle seat 10 relating to the present embodiment, vibrations can be imparted to the driver by using the airbags 30 that are used for massaging (refreshing). Accordingly, in the vehicle seat 10 that is provided with the airbags 30 for massaging (refreshing), there is no need to provide a vibration generating device separately from the airbags 30, and the occurrence of the problem of space for setting this vibration generating device being insufficient, and the problem of the manufacturing cost increasing due to this vibration generating device, can be prevented.

Further, in accordance with the present embodiment, as described above, because there is no need to provide a vibration generating device within the seatback 14 or within the seat cushion 12 of the vehicle seat 10, the thicknesses of the seat pads 22 within the seatback 14 and within the seat cushion 12 can be ensured. Accordingly, the problem of a deterioration in the seating comfort of the driver also does not arise.

Although the vehicle seat 10 relating to the present embodiment has been described above on the basis of the drawings, the vehicle seat 10 relating to the present embodiment is not limited to the illustrated structure, and the design thereof can be changed appropriately within a scope that does not depart from the gist of the present disclosure. For example, there may be a structure in which the awakening mode is executed continuously for a constant time, rather than being executed at a predetermined timing.

Further, although there is a structure in which the electromagnetic valve 32 is provided per airbag 30, embodiments are not limited to this, and there may be a structure in which several airbags 30 are connected to one of the electromagnetic valves 32. Namely, there may be a structure in which several of the airbags 30 among the plural airbags 30 vibrate simultaneously.

Further, the driver may be massaged by the airbags 30 that vibrate in the awakening mode, and it suffices for the airbags 30 to be provided at least at the interior of the seatback 14. Further, embodiments are not limited to the imparting of an awakening effect to the driver, and, for example, in the self-driving vehicle 60 shown in FIG. 7, an awakening effect may be imparted to a vehicle occupant who is seated in the rear seat or in the front passenger's seat who is scheduled to be driving next.

Further, embodiments are not limited to a structure in which the awakening mode is executed automatically on the basis of state information of the driver that is detected by a state detecting device. For example, there may be a structure in which the awakening mode is executed (manually) by a vehicle occupant who is seated in a rear seat or the front passenger's seat turning a switch (not shown) on.

Moreover, although the present embodiment is a structure in which the airbag driving device 40 is provided at the interior of the vehicle seat 10, embodiments are not limited to this, and may be structured such that the airbag driving device 40 is provided at the exterior of the vehicle seat 10 (e.g., at the lower surface of the seat cushion 12 or the rear surface of the seatback 14 or the like). Further, there may be a structure in which only the pump 56 of the air supplying/discharging device 50, or only the control device 58, is provided at the exterior of the vehicle seat 10.

What is claimed is:

1. A vehicle seat comprising:
    a plurality of airbags for massaging that are provided at least at an interior of a seatback, and that inflate to push against portions of a body of a seated vehicle occupant when the occupant is seated in the vehicle seat;
    an air supplying/discharging device that has a forced-air source that includes a pump and that feeds air under pressure, and a control valve that supplies and discharges the air, that has been fed under pressure from the forced-air source, to the plurality of airbags respectively, so that the air supplying/discharging device inflates and contracts the plurality of airbags individually; and
    an electronic control unit that, in a state in which the forced-air source is operated, repeats, at a uniform cycle, supplying and discharging of the air by switching of the control valve, to generate awakening vibrations at least at one airbag among the plurality of airbags, wherein
    to generate the awakening vibrations, the electronic control unit controls the pump to supply the air continuously to the control valve while controlling the control valve to alternately supply the air to and discharge the air from the at least one airbag.

2. The vehicle seat of claim 1, wherein the electronic control unit generates the awakening vibrations at the at least one airbag when it is detected that the seated vehicle occupant is tending toward falling asleep.

3. The vehicle seat of claim 1, wherein the electronic control unit generates the awakening vibrations at the at least one airbag at a time of an automatic driving mode of a self-driving vehicle, when it is detected that the seated vehicle occupant is tending toward falling asleep or is in a state of falling asleep.

4. The vehicle seat of claim 1, wherein the electronic control unit vibrates the plurality of airbags with the awakening vibrations at a predetermined timing and in a predetermined order.

5. The vehicle seat of claim 1, wherein the electronic control unit vibrates the plurality of airbags with the awakening vibrations at a predetermined timing and in a random order.

6. The vehicle seat of claim 1, wherein the electronic control unit controls the control valve to supply and discharge the air to/from the at least one airbag to generate the awakening vibrations at a first frequency that is higher than a second frequency at which the electronic control unit controls the control valve to supply and discharge the air to/from the at least one airbag to generate massaging vibrations.

7. The vehicle seat of claim 1, wherein the electronic control unit controls the control valve to maintain the at least one airbag in an inflated state while generating the awakening vibrations for a first time period that is shorter than a second time period at which the electronic control unit controls the control valve to maintain the at least one airbag in the inflated state while generating massaging vibrations.

8. The vehicle seat of claim 1, wherein
    to generate the massaging vibrations, the electronic control unit controls the pump to supply the air to the control valve while controlling the control valve to supply the air to the at least one airbag, but controls the pump to stop the supply of the air to the control valve while controlling the control valve to discharge the air from the at least one airbag.

9. A vehicle seat comprising:
    a plurality of airbags for massaging that are provided at least at an interior of a seatback, and that inflate to push against portions of a body of a seated vehicle occupant when the occupant is seated in the vehicle seat;
    an air supplying/discharging device that has a forced-air source that feeds air under pressure, and a control valve that supplies and discharges the air, that has been fed under pressure from the forced-air source, to the plurality of airbags respectively, so that the air supplying/discharging device inflates and contracts the plurality of airbags individually; and
    an electronic control unit that, in a state in which the forced-air source is operated, repeats, at a uniform cycle, supplying and discharging of the air by switching of the control valve, to generate awakening vibrations at least at one airbag among the plurality of airbags, wherein
    the electronic control unit controls the control valve to supply and discharge the air to/from the at least one airbag to generate the awakening vibrations at a first frequency that is higher than a second frequency at which the electronic control unit controls the control valve to supply and discharge the air to/from the at least one airbag to generate massaging vibrations.

* * * * *